(12) United States Patent
Moriyama

(10) Patent No.: US 7,303,734 B2
(45) Date of Patent: *Dec. 4, 2007

(54) ENDOSCOPE CONTAINER FOR HIGH-PRESSURE STEAM STERILIZATION

(75) Inventor: Hiroki Moriyama, Akishima (JP)

(73) Assignee: Olympus Corporation, Tokyo (JP)

( * ) Notice: Subject to any disclaimer, the term of this patent is extended or adjusted under 35 U.S.C. 154(b) by 520 days.

This patent is subject to a terminal disclaimer.

(21) Appl. No.: 09/919,190

(22) Filed: Jul. 31, 2001

(65) Prior Publication Data
US 2002/0015673 A1    Feb. 7, 2002

(30) Foreign Application Priority Data
Aug. 4, 2000    (JP)    ............... 2000-237312

(51) Int. Cl.
*A61L 2/00*    (2006.01)
(52) U.S. Cl. ............ 422/297; 134/170; 422/292; 422/294
(58) Field of Classification Search ........ 422/292, 422/294, 297, 300; 134/170
See application file for complete search history.

(56) References Cited

U.S. PATENT DOCUMENTS

| 3,633,758 A | * | 1/1972 | Morse et al. ............ 211/85.13 |
| 5,534,221 A | * | 7/1996 | Hillebrenner et al. ......... 422/33 |
| 5,759,490 A | * | 6/1998 | Malchesky .................... 422/28 |
| 5,882,589 A | * | 3/1999 | Mariotti ........................ 422/28 |
| 6,361,751 B1 | * | 3/2002 | Hight, III .................... 422/292 |

FOREIGN PATENT DOCUMENTS

| JP | 5-285103 | | 11/1993 |
| JP | 06-063007 | | 3/1994 |
| JP | 2000-060791 | * | 2/2000 |

* cited by examiner

*Primary Examiner*—Krisanne Jastrzab
(74) *Attorney, Agent, or Firm*—Scully, Scott, Murphy & Presser P.C.

(57) ABSTRACT

An endoscope container for high-pressure steam sterilization in accordance with the present invention consists mainly of a tray, a lid member, and a positioning member. The tray serves as a housing and has a plurality of pores. The lid member blocks the opening of the tray and has a plurality of pores. The positioning member is formed in one of the tray and lid member, and restricts bending of a predetermined portion of an insertion member having a soft part so that the bend radius of the predetermined portion thereof will be larger than the bend radius of the other portion thereof.

16 Claims, 7 Drawing Sheets

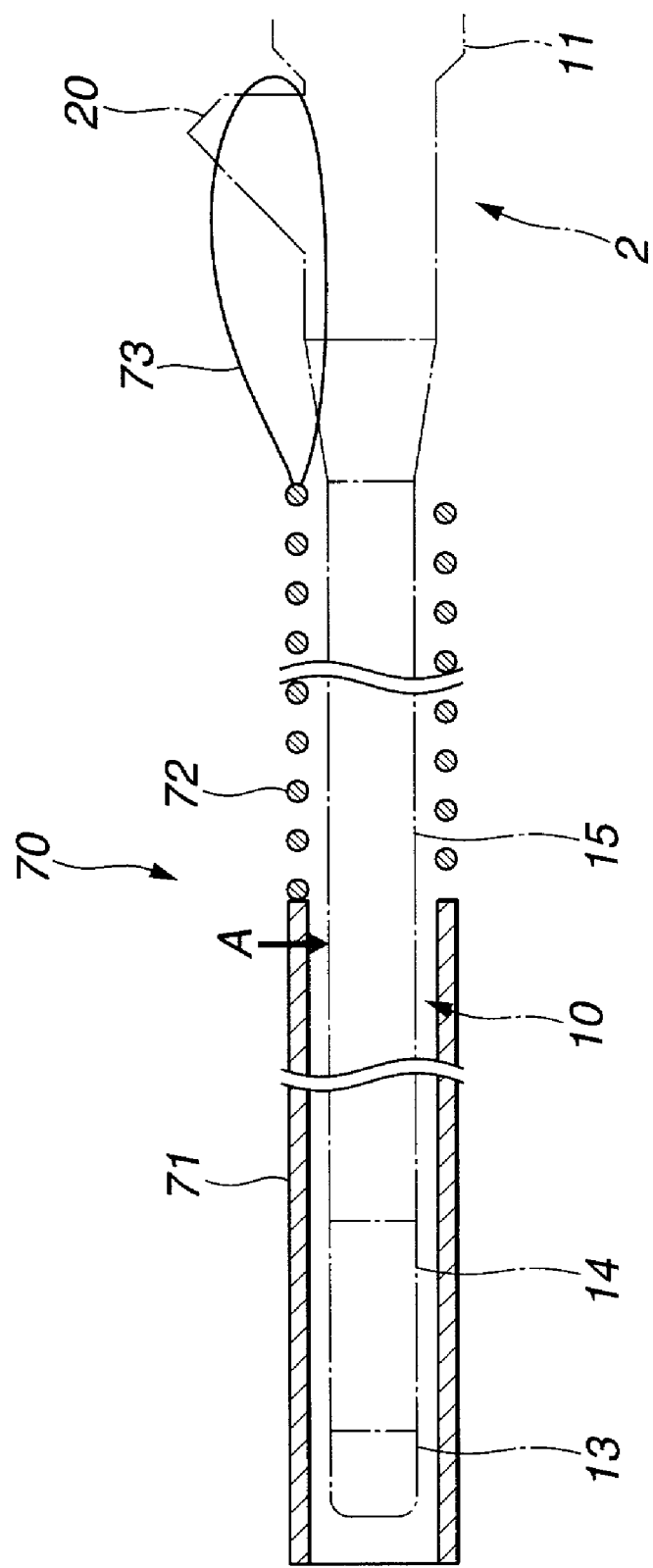

ENDOSCOPE CONTAINER FOR HIGH-PRESSURE STEAM STERILIZATION

This application claims benefit of Japanese Application No. 2000-237312 filed in Japan on Aug. 4, 2000 the contents of which are incorporated by this reference.

BACKGROUND OF THE INVENTION

1. Field of the Invention

The present invention relates to an endoscope container for high-pressure steam sterilization in which an endoscope is stowed for high-pressure steam sterilization.

2. Description of the Related Art

Medical endoscopes have been widely used in the past. An elongated insertion member of such a medical endoscope is inserted into a body cavity in order to observe an intracavitary organ or the like. If necessary, therapeutic accessories may be passed through a therapeutic accessory channel that runs through the medical endoscope in order to perform various cures.

The endoscope for use in the field of medicine has an insertion member thereof inserted into a body cavity for the purpose of observing an organ. Otherwise, therapeutic accessories may be inserted into a therapeutic accessory channel that runs through the endoscope in order to perform various cures or treatments.

A user may use an endoscope or therapeutic accessories, and want to reuse the endoscope or therapeutic accessories for another patient. However, medical equipment must be cleaned and disinfected after being used for examination or treatment. This is essential to prevent inter-patient infection by way of an endoscope or therapeutic accessory.

In recent years, autoclaving has become a mainstream method of disinfecting or sterilizing medical equipment. This is attributable to the fact that autoclaving is not labor-intensive but is low-cost and that equipment becomes reusable immediately after being autoclaved.

For example, Japanese Unexamined Patent Publication No. 5-285103 has disclosed an autoclave for endoscopes that autoclaves an endoscope without adversely affecting the capabilities of the endoscope.

An environment for high-pressure steam sterilization is very severe for an endoscope that is a piece of precise medical equipment. In order to realize an endoscope that withstands the conditions for high-pressure steam sterilization, measures are taken against high pressure, high temperature, and steam. Incidentally, this point is not taken into consideration in realizing an endoscope that is supposed to be reused after being disinfected or sterilized using an ordinary means.

However, as far as an endoscope whose insertion member has a soft part is concerned, since the insertion member is long, the endoscope must be settled in a high-pressure steam sterilizer with the insertion member rounded. If the endoscope is sterilized with high-pressure steam in this state, the soft part of the insertion member is held bent as it is rounded. When the endoscope is used to perform examination after sterilized with high-pressure steam, the inserting smoothness of the insertion member of the endoscope deteriorates due to the bent state of the soft part.

SUMMARY OF THE INVENTION

Accordingly, an object of the present invention is to provide an endoscope container for high-pressure steam sterilization that prevents deterioration of inserting smoothness attributable to the fact that when the endoscope is sterilized with high-pressure steam, a soft part of the endoscope is held bent due to high-pressure steam.

Briefly, according to the present invention, there is provided an endoscope container for high-pressure steam sterilization consisting mainly of a tray, a lid member, and a positioning member. The tray serves as a housing and has a plurality of pores. The lid member has a plurality of pores and blocks the opening of the tray. The positioning member is included in either of the tray or lid member, and restricts bending of a predetermined portion of an insertion member having a soft part so that the bend radius of the predetermined portion of the insertion member will be larger than the bend radius of the other portion thereof. Consequently, the soft part of the insertion member of the endoscope is prevented from being held bent.

BRIEF DESCRIPTION OF THE DRAWINGS

FIG. 1 to FIG. 3 are explanatory diagrams showing a first embodiment of the present invention;

FIG. 1 shows the overall configuration of an endoscope system;

FIG. 2 shows an endoscope settled in a sterilization casing that is an example of an endoscope container for high-pressure steam sterilization;

FIG. 4 and FIG. 5 are explanatory diagrams showing a second embodiment of the present invention;

FIG. 4 shows another structure of a sterilization casing;

FIG. 8 is an explanatory diagram showing another structure of an endoscope container for high-pressure steam sterilization in accordance with a third embodiment of the present invention.

DESCRIPTION OF THE PREFERRED EMBODIMENTS

Figure 1:
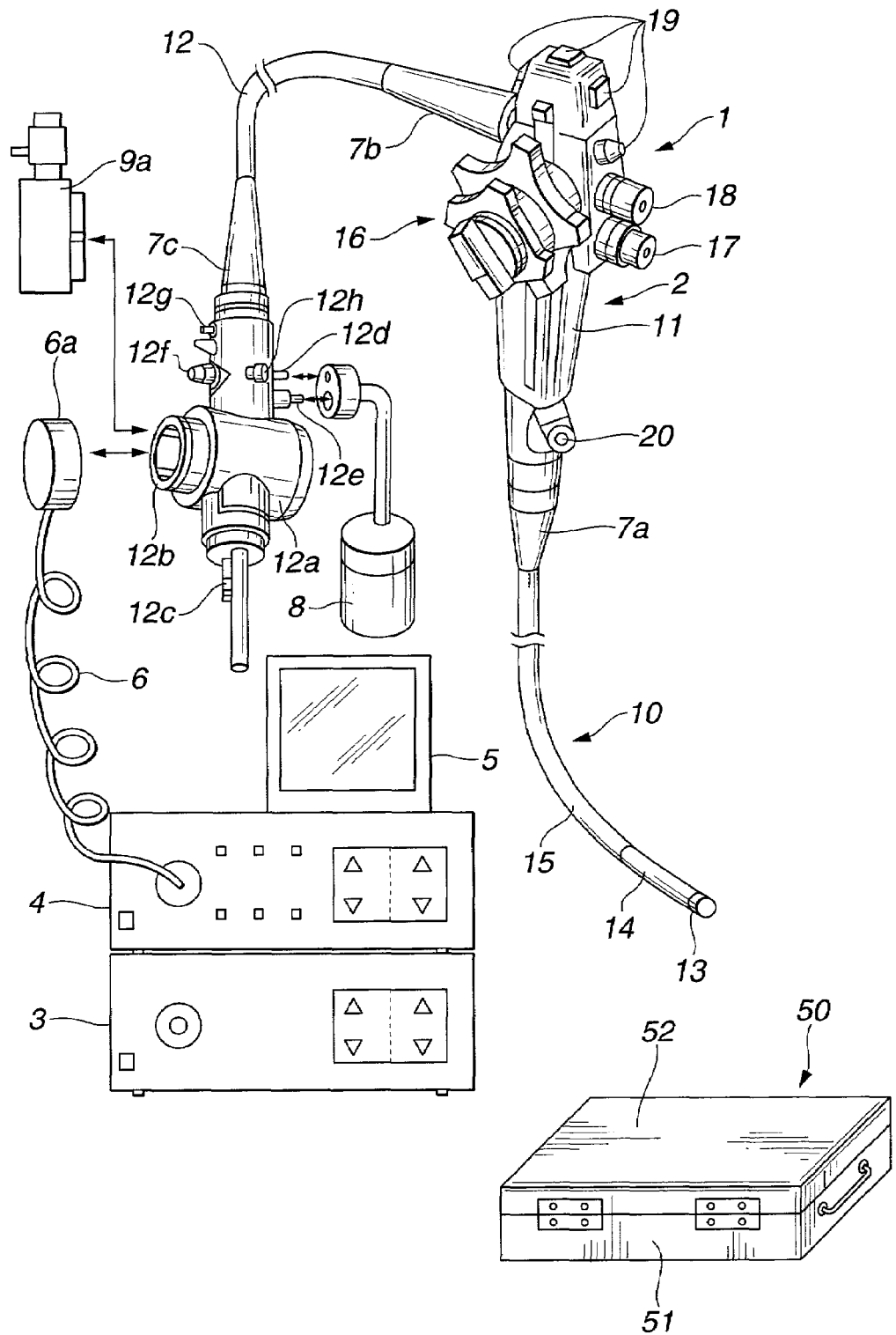

Referring to the drawings, embodiments of the present invention will be described below.

A first embodiment of the present invention will be described with reference to FIG. 1 to FIG. 3B.

As shown in FIG. 1, an endoscope system 1 in which the present embodiment is employed consists mainly of an electronic endoscope (hereinafter simply an endoscope) 2, a light source apparatus 3, a video processor 4, and a monitor 5.

The endoscope 2 has an imaging means. The light source apparatus 3 supplies illumination light to the endoscope 2. The video processor 4 controls the imaging means, and processes an image signal produced by the imaging means to produce, for example, a video signal. The video processor 4 is connected to the monitor 5. A sterilization casing 50 that will be described later is an endoscope container for high-pressure steam sterilization in which the endoscope 2 is stowed.

The endoscope 2 consists mainly of an insertion member 10, a control section 11, and a universal cord 12. The insertion member 10 is elongated and flexible. The control section 11 is coupled to the proximal end of the insertion member 10. The universal cord 12 is flexible and extended from the lateral part of the control section 11.

A connector 12a that can be freely connected to or disconnected from the light source apparatus 3 is fixed to an end of the universal cord 12. When the connector 12a is connected to the light source apparatus 3, illumination light emanating from a lamp (not shown) that is incorporated in the light source apparatus 3 is propagated to a light guide (not shown) and runs through the endoscope 2. A region to be observed is thus illuminated.

An anti-breakage member 7a for an insertion member formed with an elastic member is mounted on a joint between the insertion member 10 and control section 11 in order to prevent abrupt bending. Likewise, an anti-breakage member 7b for a control member analogous to the anti-breakage member 7a for an insertion member is mounted on a joint between the control section 11 and universal cord 12. Moreover, an anti-breakage member 7c for a connector analogous to the anti-breakage member 7a for an insertion member is mounted on a joint between the universal cord 12 and connector 12a.

The insertion member 10 of the endoscope 2 that is elongated and flexible has a distal rigid part 13, a bending section 14, and a flexible tube 15, which is a soft part, coupled to one another in that order from the distal end of the insertion member.

The distal rigid part 13 is formed with a hard member. An observation window and an illumination window (not shown) are formed in, for example, the distal surface of the distal rigid part 13. Otherwise, an aeration/perfusion nozzle from which cleaning fluid or gas is jetted out towards the observation window, and a suction port through which a humor or filth is sucked are exposed on the distal surface of the distal rigid part 13.

The bending section 14 has a plurality of bending pieces (not shown) concatenated so that the bending section 14 can be bent freely.

The flexible tube 15 is soft and resilient and has delicate properties.

An angling knob 16 is formed on the control section 11. By manipulating the angling knob 16, the bending section 14 is bent in desired directions. In other words, when the bending section 14 is bent, the distal surface of the distal rigid part 13 having the observation window formed therein is angled in desired directions.

In addition to the angling knob 16, an aeration/perfusion button 17, a suction button 18, a plurality of remote control switches 19, and a therapeutic accessory insertion port 20 are formed on the control section 11.

By pressing the aeration/perfusion button 17, cleaning liquid or gas is jetted out from the aeration/perfusion nozzle. By pressing the suction button 18, a humor etc. can be sucked through the suction port. The plurality of remote control switches 19 is used to remotely control, for example, the video processor 4. The therapeutic accessory insertion port 20 communicates with a therapeutic accessory channel tube that will be described later and that runs through the insertion member of the endoscope 2.

An electric connector member 12b is formed on the lateral part of the connector 12a. A signal connector 6a fixed to a signal cord 6 that is coupled to the video processor 4 is joined with the electric connector member 12b so that the signal connector 6a can be freely connected or disconnected. The signal connector 6a is coupled to the video processor 4, whereby the imaging means in the endoscope 2 is controlled by the video processor. Moreover, an image signal sent from the imaging means is processed in order to produce a video signal. Consequently, an endoscopic view image is displayed on the screen of the monitor 5.

The electric connector member 12b has an air vent hole that is not shown and that links the interior and exterior of the endoscope 2. Therefore, a pressure regulating valve-inclusive waterproof cap (hereinafter simply a waterproof cap) 9a having a pressure regulating valve (not shown) that blocks the air vent hole can be freely detachably attached to the electric connector member 12b of the endoscope 2.

The connector 12a has a gas supply base 12c, a water supply tank pressurization base 12d, a fluid supply base 12e, a suction base 12f, an injection base 12g, and a ground base 12h formed thereon.

The gas supply base 12c is freely connected and disconnected to/from a gas source (not shown) that is incorporated in the light source apparatus 3 (not shown). The water supply tank pressurization base 12d and liquid supply base 12e are connected to a water tank 8, which is a liquid source, so that they can be connected and disconnected freely. The suction base 12f is connected to a sucking device (not shown) to suck fluid through the suction port. The injection base 12g is connected to a water supplying device (not shown) that supplies water. An electric cable is plugged in to the ground base 12h, whereby high-frequency leakage current generated during diathermy is fed back to a diathermy device (not shown).

The endoscope 2 can be cleaned after being used for observation or treatment. The endoscope 2 can then be sterilized with high-pressure steam. Before the endoscope 2 is sterilized with high-pressure steam, the waterproof cap 9a is attached to the electric connector member 12b. Moreover, in order to sterilize the endoscope 2 with high-pressure steam, the endoscope 2 is stowed in the sterilization casing 50.

The sterilization casing 50 consists mainly of a tray 51 that serves as a housing and a lid member 52 that blocks the opening of the tray 51. The tray 51 has a positioning member that is shaped in conformity with the shape of the endoscope. The positioning member restricts the locations of the components of the endoscope 2 so that the insertion member 10, control section 11, universal cord 12, and connector 12a of the endoscope 2 will be settled in predetermined places. Moreover, the tray 51 and lid member 52 each have a plurality of pores through which high-pressure steam is led in to the casing. When the lid member 52 is closed to meet the tray 51, the interior of the casing is by no means airtight.

Now, the sterilization casing 50 will be described with reference to FIG. 2 and FIG. 3.

Figure 2:
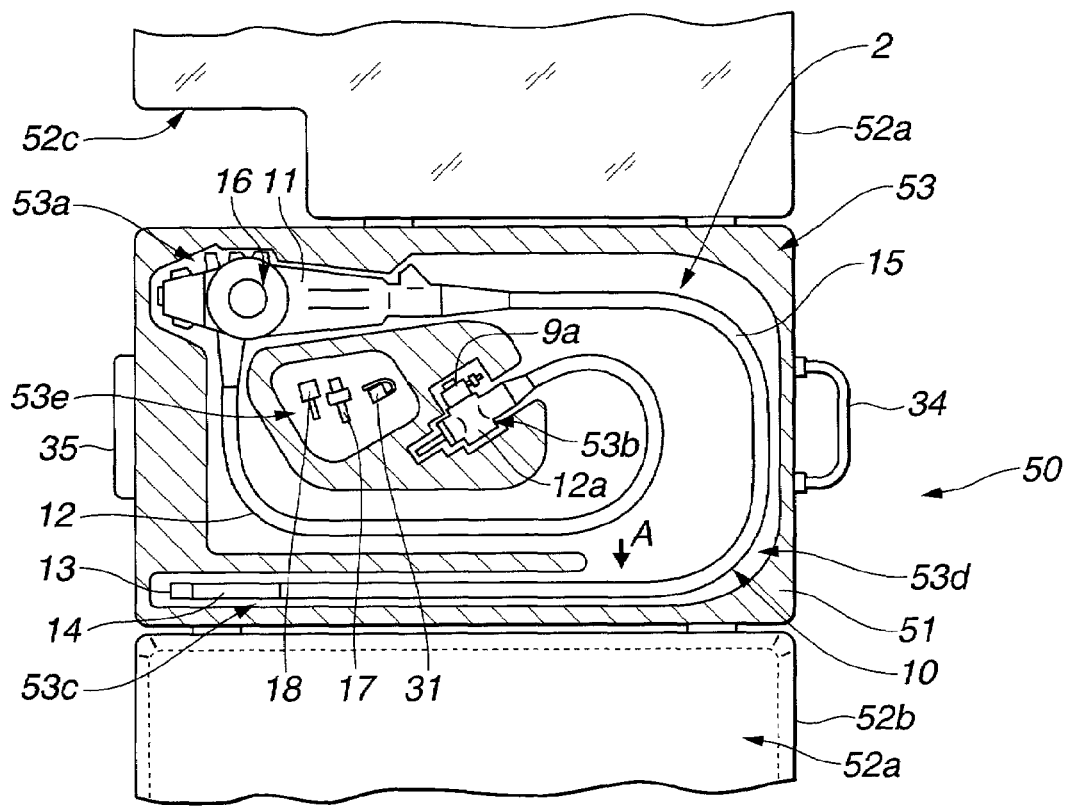

As shown in FIG. 2, the sterilization casing 50 has a tray body 53 that composes the tray 51. The tray body 53 is attached by the lid member 52 that can be opened or closed freely and is composed of an inner lid 52a shaped like a thin plate and an outer lid 52b serving as a housing. In the present embodiment, the inner lid 52a and outer lid 52b are hinged to opposed sides of the tray body 52 to open in opposite directions. Moreover, the lid member 52 has the inner lid 52a and outer lid 52b closed in that order. Even when an attempt is made to close the outer lid 52b and inner lid 52a in that order, the lids will not be closed.

The flexible tube 15 of the endoscope 2 is available in various lengths. The present embodiment is concerned with the flexible tube 15 of a long type. When the flexible tube of a long type is adopted, unless the insertion member 10 and universal cord 12 are bent, the endoscope cannot be settled in a relatively small high-pressure steam sterilizer that sterilizes the endoscope 2.

Therefore, the tray body 53 has concave parts 53a, 53b, and 53c that constitute a positioning member which enables the control section 11, the connector 12a, and the predetermined portion of the insertion member 10 to settle into predetermined places. The control section 11, the connector 12a, and the distal rigid part 13 of the insertion member 10 are settled into the concave parts 53a, 53b, and 53c that are the predetermined places. Consequently, the bent states of the universal cord 12 and insertion member 10, that is, the stowed states thereof are determined as shown in FIG. 2.

Specifically, the tray body 53 has the concave control-section part 53a, the concave connector part 53b, the concave predetermined-portion part 53c, a stowage 53d, and a small-articles stowage 53e. The concave control-section part 53a provides a stowage for the control section 11 and is part a positioning member which restricts the location of the control section 11. The concave connector part 53b provides a stowage for the connector 12a and is part of the positioning member which restricts the location of the connector 12a. The concave predetermined-portion part 53c provides a stowage for the predetermined portion of the insertion member 10 including the distal rigid part 13 and is part of the positioning member which restricts the location of the predetermined portion. The stowage 53d is a place in which the universal cord 12 of the endoscope 2 and the portion of the insertion member 10 other than the predetermined portion thereof are stowed. The small-articles stowage 53e is a place in which small articles such as the aeration/perfusion operation button 17 that was removed from the endoscope 2, the suction button 18, including a therapeutic accessory plug 31 that has been attached to the therapeutic accessory insertion port 20, are stowed.

Incidentally, the predetermined portion of the insertion member is a portion that dominates the inserting smoothness thereof. According to the present embodiment, the predetermined portion of the insertion member includes the distal rigid part 13, the bending section 14, or the distal portion of the flexible tube 15.

When an endoscope dedicated to the lower-part digestive tract is adopted, the flexible tube 15 of the endoscope is as long as, for example, 133 cm or 168 cm. However, generally, when the insertion member of an endoscope is inserted from the anus to the cecum while efforts are made not to create an excessive sag, or in other words, when the insertion member is advanced the shortest possible distance, the length of the inserted portion of the insertion member is approximately 70 cm.

In other words, the distal portion of 70 cm long of the insertion member is inserted to almost all patients. The inserted portion of approximately 70 cm long of the insertion member is the predetermined portion including a portion of the soft part. The concave parts 53a, 53b, 53c, and 53d of the tray body 53 are formed so that the predetermined portion of the insertion member will be stowed in a substantially straight form or a quite loosely bent form that is close to the straight form, that is, in a curved form that exhibits a large bend radius. Consequently, when the endoscope 2 is stowed with the components thereof placed in the concave parts 53a, 53b, 53c, and 53d of the tray body 53, the insertion member 10 is stowed in an illustrated form. Namely, a point of arrow A indicated in FIG. 2 is a point located approximately 70 cm away from the distal end of the distal rigid part 13. When the endoscope 2 is stowed in this way, the predetermined portion including a portion of the soft part is stowed in a substantially straight form.

Incidentally, the concave parts 53a, 53b, and 53c have dimensions larger than the outer dimensions of the control section 11, connector 12a, distal rigid part 13, bending section 14, and flexible tube 15 so that a predetermined clearance will be preserved in each of the concave parts. Herein, the clearances in the concave parts are determined so that the control section 11, the connector 12a, the distal rigid part 13, bending section 14, and the distal portion of the flexible tube 15 will not move largely, can be mounted or dismounted easily, and will be fully exposed to high-pressure steam.

Moreover, the depths of the concave parts 53a, 53b, and 53d are determined so that the control section 11, connector 12a, insertion member 10, and universal cord 12 will not jut out of the top of the tray body 53.

However, when the control section 11 is put in the concave control-section part 53a, the angling knob 16 juts out of the top of the tray body 53. All the portions of the control section 11 except the angling knob 16, the connector 12a, the distal rigid part 13, the bending section 14, the flexible tube 15, and the universal cord are fully settled in the concave parts 53a, 53b, 53c, and 53d.

Furthermore, the concave parts 53a and 53b are shaped to have the clearances preserved so that an attempt of stowing the endoscope 2 in the tray body 53 with the aeration/perfusion button 17, suction button 18, and therapeutic accessory plug 31 attached to the endoscope 2 will fail. Herein, the aeration/perfusion button 17, suction button 18, and therapeutic accessory plug 31 are freely attachable and detachable to/from the endoscope 2.

In other words, when the aeration/perfusion button 17, suction button 18, and therapeutic accessory plug 31 are detached from the endoscope, the endoscope can be stowed in the tray body 53. At this time, high-pressure steam used for high-pressure steam sterilization fully permeates the channels running through the endoscope 2 and the joints between the endoscope 2 and the aeration/perfusion button 17, suction button 18, and therapeutic accessory plug 31 respectively.

Figure 3A:
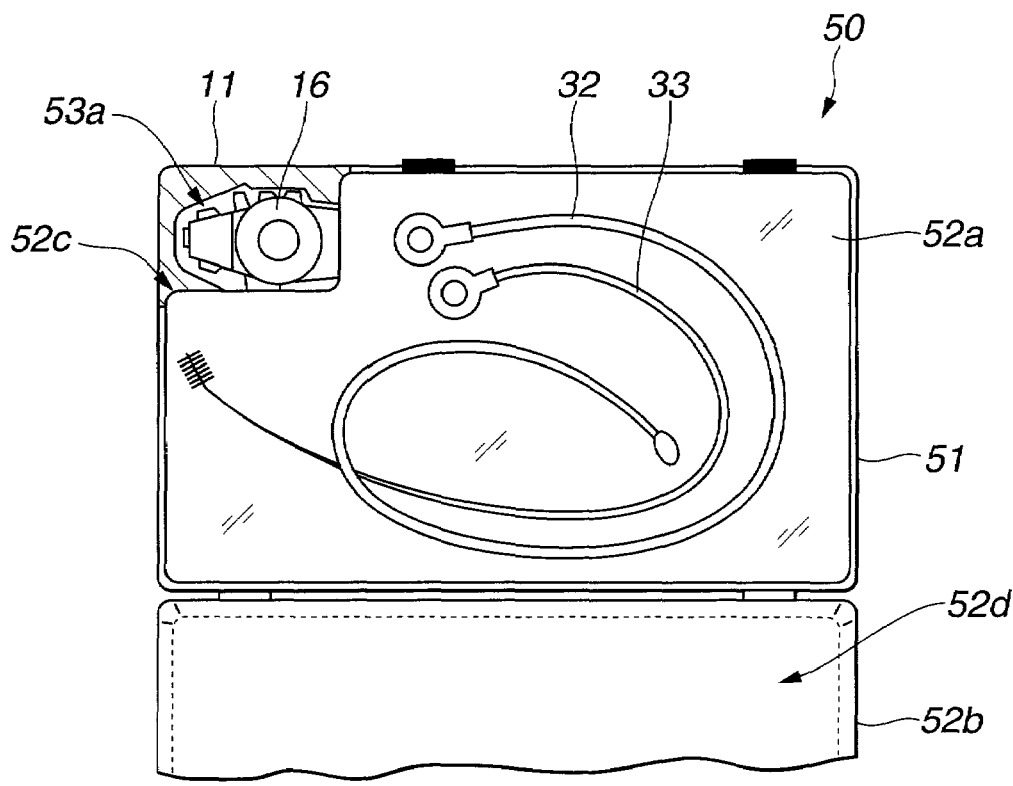
FIG. 3A shows the sterilization casing with a tray body covered with an inner lid.

As shown in FIG. 3A, the inner lid 52a shaped like a thin plate and included in the sterilization casing 50 has a notch 52c. When the inner lid 52a is closed to cover the top of the tray body 53, the concave parts 53a, 53b, 53c, 53d, and 53e are hidden behind the inner lid 52a. In this state, the angling operation knob 16 juts out through the notch 52c.

Moreover, when the inner lid 52a is placed on the top of the tray body 53, the insertion member 10, control section 11, and universal cord 12 of the endoscope 2 are positioned and stowed with the predetermined clearances preserved. At this time, the insertion member 10, control section 11, and universal cord 12 will not be abutted on anything other than the tray body 53 and inner lid 52a. In this state, a therapeutic accessory 32 and a cleaning tool 33 can be placed on the inner lid 52a.

Preferably, the inner lid 52a is formed with a transparent member and may be colored.

Moreover, the outer lid 52b of the sterilization casing 50 that serves as a housing has a dent 52d formed as an inner space that accommodates the therapeutic accessory 32 and cleaning tool 33.

A handle 34 and a grip 35 are formed on the outer edge of the tray body 53. The handle 34 is grabbed by the hand in order to carry the sterilization casing 50, for example, lengthwise. The grip 35 is used to hold the sterilization casing 50, for example, horizontally.

Now, a description will be made of typical conditions for sterilizing the endoscope 2 with high-pressure steam.

The conditions are stipulated in the U.S. standard ANSI/AAMI ST37-1992 approved by the American National Standards Institute (ANSI) and published from the Association for the Advancement of Medical Instrumentation (AAMI). The U.S. standard stipulates that a pre-vacuum sterilization process should be performed at 132° C. for four min, and that a gravity settling sterilization process should be performed at 132° C. for ten min.

The condition of the temperature for high-pressure steam sterilization varies depending on the type of high-pressure steam sterilizer or the time required for sterilization. In general, the temperature ranges from about 115° C. to about 138° C. However, some sterilizers can be set to about 142° C.

The condition of the time varies depending on the condition of the temperature for sterilization. In general, the time ranges from about 3 min to about 60 min. Some types of sterilizers can be set to about 100 min.

For the sterilization, the pressure in a sterilization chamber is set to a value that is higher by about 0.2 MPa than the atmospheric pressure.

Next, a typical pre-vacuum high-pressure steam sterilization process for endoscopes will be described briefly.

Figure 3B:
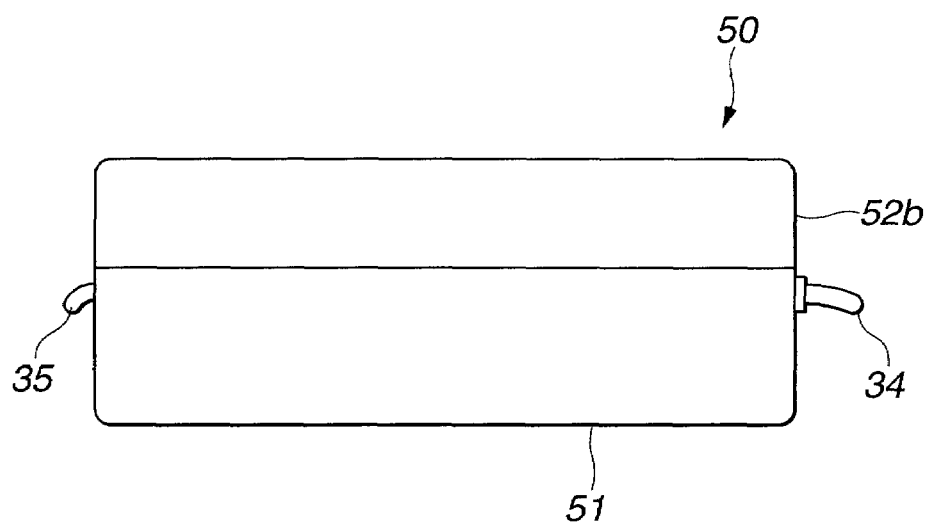
FIG. 3B shows the sterilization casing with an outer lid closed.

First, the waterproof cap 9a is attached to the electric connector member 12b of the endoscope 2 that is an apparatus to be sterilized. Thereafter, the endoscope 2 is stowed in the sterilization casing 50 with the portions thereof settled in the concave parts 53a, 53b, 53c, and 53d of the tray body 53. The aeration/perfusion button 17, suction button 18, and therapeutic accessory plug 31 are stowed in the small-articles stowage 53e. The tray body 53 is covered with the inner lid 52a. The therapeutic accessory 32 and cleaning tool 33 are placed on the inner lid 52a that covers the tray body 53. Thereafter, the outer lid 52b is closed to meet the tray body as shown in FIG. 3B. The sterilization casing 50 is then placed in a sterilizer. Prior to high-pressure sterilization, a sterilization chamber is decompressed (at a pre-vacuum step).

Since the waterproof cap 9a is attached to the electric connector member 12b, the pressure regulating valve is closed and the air vent hole is blocked. In other words, the interior of the endoscope 2 is shut out from the exterior thereof and sealed to be watertight.

The pre-vacuum step is a step of making preparations for infiltration of steam to every part of the apparatus to be sterilized at a sterilization step. The sterilization chamber is decompressed at the pre-vacuum step, whereby high-pressure high-temperature steam permeates the entire apparatus to be sterilized. For the pre-vacuum step, the pressure in the sterilization chamber is generally set to a value that is smaller by a value ranging about 0.07 MPa to about 0.09 MPa than the atmospheric pressure.

When the pressure in the sterilization chamber is decreased at the pre-vacuum step, a difference in pressure occurs between the interior and exterior of the endoscope 2, that is, the external pressure of the endoscope 2 gets lower than the internal pressure thereof. This causes the pressure regulating value of the waterproof cap 9a to open. The interior and exterior of the endoscope 2 communicate with each other through the air vent hole. Consequently, the difference in pressure between the interior and exterior of the endoscope 2 is prevented from increasing, that is, the endoscope 2 is protected from being broken due to the difference in pressure.

Next, the sterilization step of feeding high-pressure high-temperature steam into the sterilization chamber so as to sterilize the endoscope will be described below.

At the sterilization step, the sterilization chamber is pressurized. Consequently, a difference in pressure occurs between the interior and exterior of the endoscope 2, that is, the external pressure of the endoscope 2 gets higher than the internal pressure thereof. This causes the pressure regulating valve of the waterproof cap 9a to close. Eventually, high-pressure steam is disabled from invading into the endoscope through the air vent hole.

However, high-pressure steam invades into the sterilization casing 50 through the pluralities of pores formed in the tray body 53 and in the inner lid 52a and outer lid 52b respectively that constitute the lid member 52. The high-pressure steam then invades gradually into the endoscope through a sheathing tube 15c of the flexible tube 15 or O rings (not shown). The sheathing tube 15c is a housing member of the endoscope 2 and is made of a high polymer material. The O rings are made of fluorocarbon rubber or silicon rubber and serve as a sealing means included in the sheathing tube 15c and joints of housing members of the endoscope 2.

At this time, pressure directed from outside to inside is applied to the endoscope 2. The pressure is equivalent to the sum of pressure released during decompression at the pre-vacuum step and pressure added at the sterilization step.

After the sterilization step is completed, the sterilization chamber is decompressed again in order to dry the apparatus (dry step) that has been sterilized.

At the dry step, the sterilization chamber is decompressed in order to remove steam from the sterilization chamber. This facilitates drying of the endoscope 2. For the dry step, the pressure in the sterilization chamber is set to a value that is smaller by a value ranging from about 0.07 to about 0.09 MPa than the atmospheric pressure. The dry step is followed arbitrarily when needed.

At the decompression step succeeding the sterilization step, the pressure in the sterilization chamber is decreased. Consequently, a difference in pressure occurs between the interior and exterior of the endoscope 2, that is, the external pressure of the endoscope 2 gets lower than the internal pressure thereof. When the difference in pressure occurs, the pressure regulating valve of the waterproof cap 9a opens substantially at the same time. The interior and exterior of the endoscope 2 communicate with each other through the air vent hole. This prevents occurrence of a large difference in pressure between the interior and exterior of the endoscope.

When the decompression step is completed, the sterilization chamber is pressurized. A difference in pressure occurs between the interior and exterior of the endoscope 2, that is, the external pressure of the endoscope 2 gets higher than the internal pressure thereof. This causes the pressure regulating valve of the waterproof cap 9a to close.

When all the steps of high-pressure steam sterilization are completed, pressure directed from outside to inside is applied to the housing of the endoscope 2. The pressure is equivalent to pressure released at the decompression step. When the waterproof cap 9a is detached from the electric connector member 12b, the interior and exterior of the endoscope 2 communicate with each other through the air vent hole. Consequently, the internal pressure of the endoscope 2 becomes equal to the atmospheric pressure. The housing of the endoscope 2 is unloaded from the difference in pressure.

As mentioned above, at the sterilization step, the interior and exterior of the endoscope 2 are exposed to high-pressure steam. At this time, the predetermined portion of the endoscope 2 that includes the distal portion of the flexible tube 15 will not be held bent, though it is exposed to high-pressure steam. This is because the predetermined portion of the endoscope 2 of approximately 70 cm long away from the distal end of the distal rigid part 13 is stowed in a substantially straight form in the sterilization casing 50. Incidentally, even if the distal portion of the flexible tube 15 is exposed to high pressure steam, the predetermined portion of the flexible tube 15 that largely affects the inserting smoothness of the insertion member is prevented from being held bent.

As mentioned above, the positioning member including the concave control-section part, concave connector part, and concave predetermined-portion part is formed as an integral part of the tray body that forms the sterilization casing. The positioning member restricts the stowed state of the predetermined portion including the distal portion of the flexible tube to the soft part to the substantially straight form. Incidentally, the stowed state of the predetermined portion of the insertion member including the distal portion of the flexible tube largely affects the inserting smoothness of the insertion member. When the endoscope is stowed in the tray body, the predetermined portion of the insertion member having the soft part is settled in the straight form. Therefore, after the endoscope is sterilized with high-pressure steam, the predetermined portion of the insertion member the soft part will not be held bent. This means that the inserting smoothness of the insertion member will not change despite high-pressure steam sterilization.

According to the present embodiment, the predetermined portion of 70 cm long away from the distal portion of the insertion member is stowed in a substantially straight form. If a high-pressure steam sterilizer has a sufficient space, the length of the distal portion of the insertion member that is stowed in the straight form may be larger than 70 cm.

A second embodiment of the present invention will be described with reference to FIG. 4 to FIG. 5C below.

Figure 4:
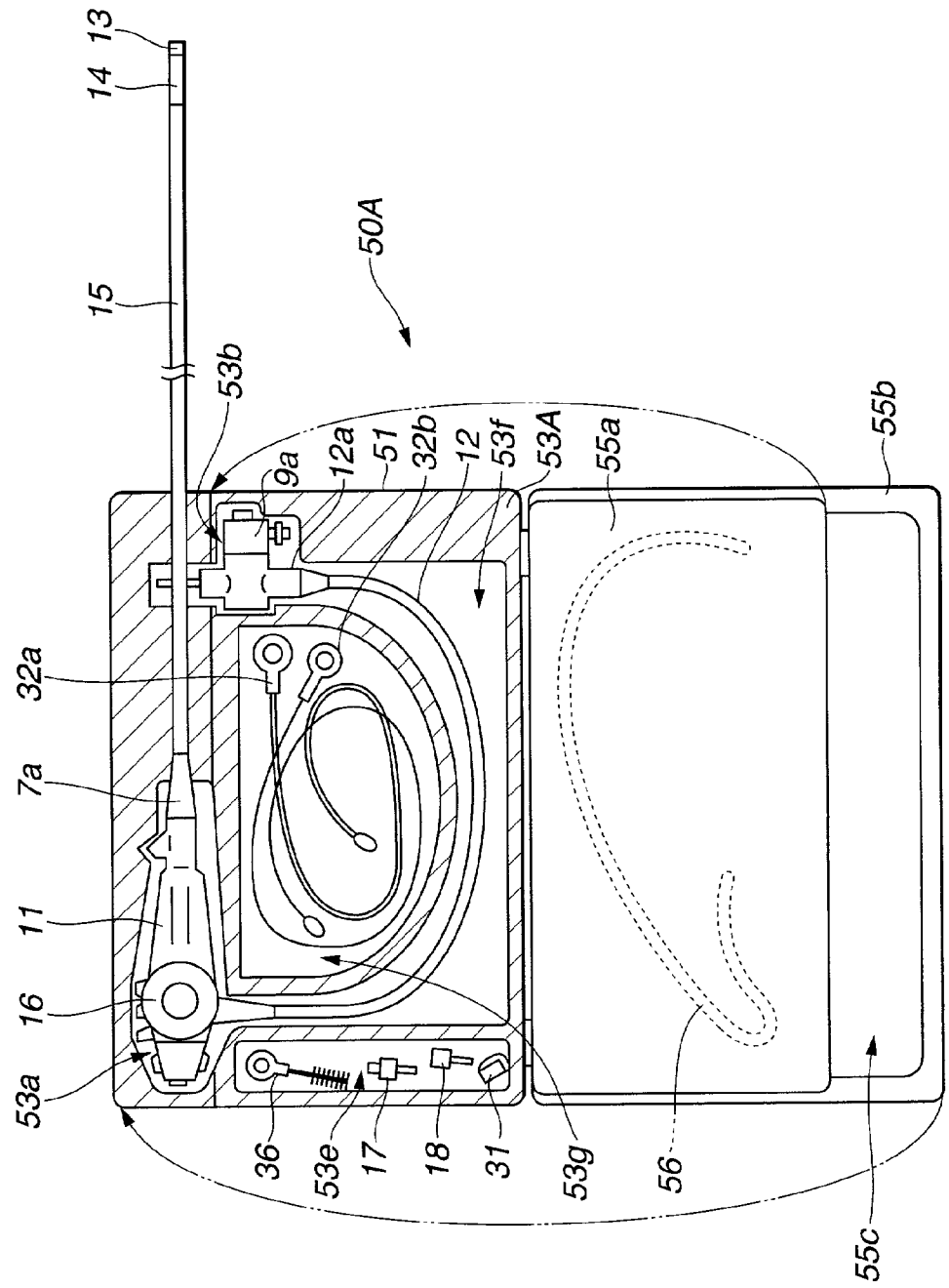

As shown in FIG. 4, a sterilization casing 50A in accordance with the present embodiment consists mainly of a tray body 53A, an inner lid 55a, and an outer lid 55b. The inner lid 55a is hinged to one side of the tray body 53A and freely opened or closed as indicated with an alternate long and two short dashes line. The outer lid 55b is freely opened or closed as indicated with an alternate long and two short dashes line. A concave control-section part 53a, a concave universal-cord part 53f, a concave connector part 53b, a small-articles stowage 53e, and a therapeutic accessory stowage 53g are formed as integral parts of the tray body 53A. The control section 11, universal cord 12, and connector 12a of the endoscope 2 are settled in the concave control-section part 53a, concave universal-cord part 53f, and concave connector part 53b respectively. The aeration/perfusion button 17, the suction button 18, the therapeutic accessory plug 31, and a cleaning brush 36 are settled in the small-articles stowage 53e. Therapeutic accessories 32a and 32b are settled in the therapeutic accessory stowage 53g. According to the present embodiment, the inner lid 55a and outer lid 55b hinge on the same side of the tray body 53 to open in the same direction.

The inner lid 55a covers part of the top of the tray body 53A defined with a solid bold line in FIG. 4. When the inner lid 55a is closed to cover the tray body 53, the concave parts 53e, 53f, and 53g and part of the concave connector part 53b are hidden behind the inner lid 55a. The universal cord 12 and connector 12a of the endoscope 2 are positioned with predetermined clearances preserved in concave parts but are not abutted on anything other than the tray body 53A and inner lid 55a.

When the control section 11, universal cord 12, and connector 12a of the endoscope 2 are settled in the concave parts 53a, 53f, and 53b respectively, the insertion member 10 is placed on the tray body 53A with a majority thereof jutted out of the tray body 53A.

Figure 5A:
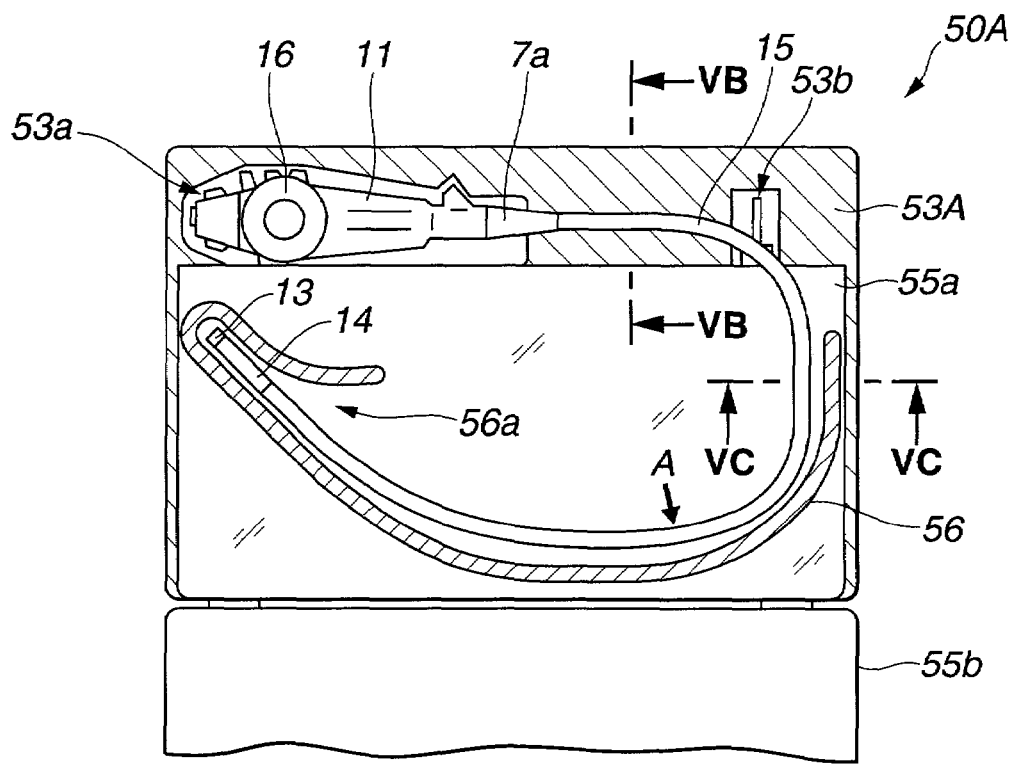
FIG. 5A is an explanatory diagram showing the sterilization casing with an insertion member placed on a closed inner lid.

In this state, the inner lid 55a is closed. Consequently, the concave parts 53e, 53f, and 53g and part of the concave connector part 53b are hidden behind the inner lid 55a. Thereafter, as shown in FIG. 5A, the insertion member 10 jutting out of the tray body 53A is placed along a curved wall 56 formed on the top of the inner lid 55a. The curved wall 56 is the positioning member and exhibits a bend radius of a predetermined value. Consequently, the distal portion of the soft part of the insertion member 10 is quite loosely bent. The bend radius of the curved wall 56 is set larger than a bend radius of the proximal portion of the insertion member.

Figure 5B:
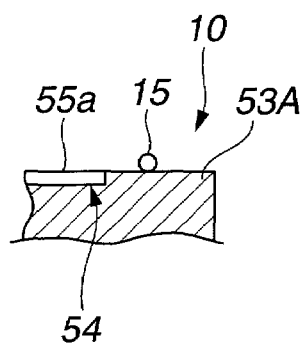
FIG. 5B is a VB-VB sectional view of the sterilization casing shown in FIG. 5A.

At this time, the inner lid 55a is, as shown in FIG. 5B, engaged with a step portion 54 of the tray body 53. Therefore, the top of the lid 55a and the top of the tray body 53A lie substantially on the same plane. The flexible tube 15 included in the insertion member 10 will therefore pass no step when being led from the tray body 53A to the inner lid 55a.

As shown in FIG. 5A, the curved wall 56 forms a distal portion-of-insertion member placement section 56a in which the distal rigid part 13 and bending section 14 of the insertion member 10 are placed with a predetermined clearance preserved in the placement section. When the distal rigid part 13 and bending section 14 of the insertion member 10 are placed in the distal portion-of-insertion member placement section 56a, the flexible tube 15 is settled along the curved wall 56.

Figure 5C:
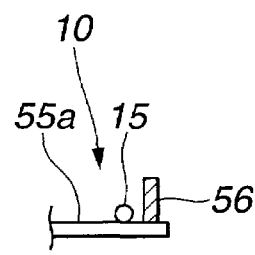
FIG. 5C is a VC-VC sectional view of the sterilization casing shown in FIG. 5A.

The height of the curved wall 56 is, as shown in FIG. 5C, larger than the diameter of the flexible tube 15. When the outer lid 55b is closed to meet the tray body 53, the flexible tube 15 and curved wall 56 on the inner lid 55a are locked in a dent 55c formed in the outer lid 55b. Consequently, when the outer lid 55b is closed, the insertion member 10 will not be pressed by the inner surface of the outer lid 55b.

According to the present embodiment, the insertion member 10, universal cord 12, and connector 12a are positioned three-dimensionally in the sterilization casing 50A with the insertion member 10 separated from the universal cord 12 and connector 12a with the inner lid 55a between them.

An arrow A in FIG. 5A indicates a point apart by approximately 70 cm away from the distal end. According to the present embodiment, the distal portion of 70 cm long of the insertion member 10 is settled while being quite loosely bent. The other components of the present embodiment and an operation thereof are identical to those of the first embodiment. The same reference numerals are assigned to the same members, and the description of the members is omitted.

As mentioned above, the insertion member, universal cord, and connector are positioned three-dimensionally within the sterilization casing while the insertion member of the endoscope is separated from the universal cord and connector thereof with the inner lid between them. This results in the compact sterilization casing.

Moreover, when the flexible tube is stowed while being bent, the bend radius of the distal portion of 70 cm long of the insertion member is set larger than the bend radius of the proximal portion of the flexible tube that is proximal from the distal portion of 70 cm long. Even if the flexible tube may be held bent a little after being sterilized with high-pressure steam, the substantial inserting smoothness of the insertion member can be retained at a very high level. The other operation and advantage are identical to those of the first embodiment.

Figure 6:
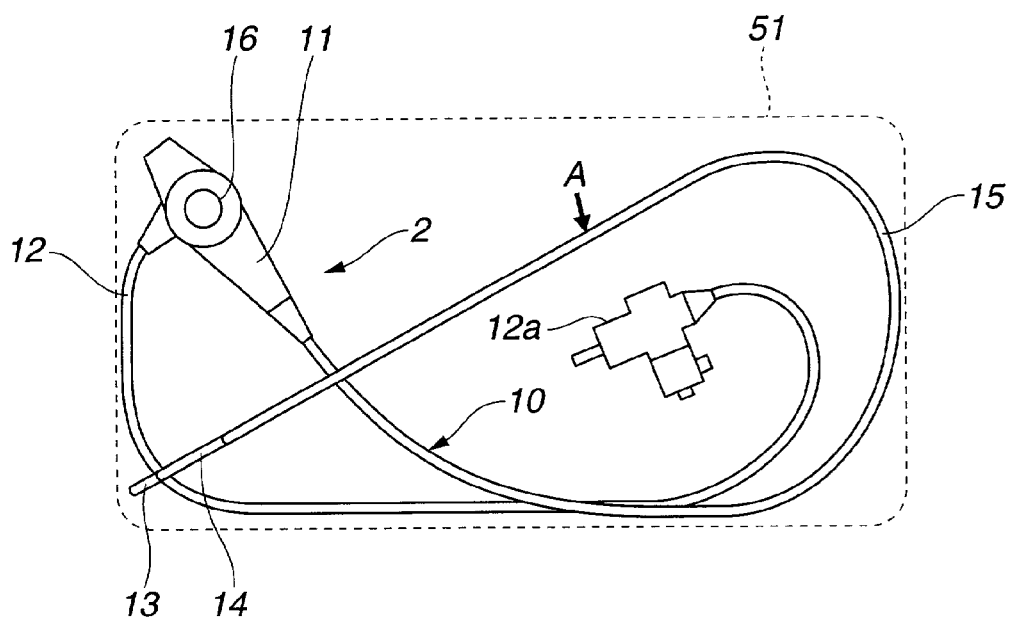
FIG. 6 is an explanatory diagram showing another form in which an endoscope is stowed.

The structure of the tray body will not be detailed. The tray body may be structured so that the endoscope 2 will be stowed as shown in FIG. 6. Specifically, according to the first embodiment, the insertion member 10 is bent along the universal cord 12 that is extended from the control section 11. According to the present embodiment, the insertion member 10 is bent in a direction different from a direction in which the universal cord 12 extends. The predetermined portion of the insertion member including a portion of the flexible tube 15 is settled this way.

At this time, the predetermined portion is settled in a substantially straight form in the direction of a diagonal of the rectangular tray 51, that is, in a direction not parallel with any side of the rectangular tray 51. Consequently, the longer part of 70 cm away from the end of the distal portion of the insertion member can be settled in the substantially straight form. Thus, the predetermined portion of the insertion member is settled along the longest possible straight line by using effectively the most of the space in the tray 51.

The endoscope 2 is angled in, normally, four directions, that is, in up, down, right, and left directions. When the angling knob 16 is manipulated, if the endoscope appears to move upwards on the screen of the monitor 5, the endoscope is said to be angled in the up direction. The other three directions are determined with respect to the up direction. According to the present embodiment, the flexible tube 15 is bent in the up direction.

Figure 7:
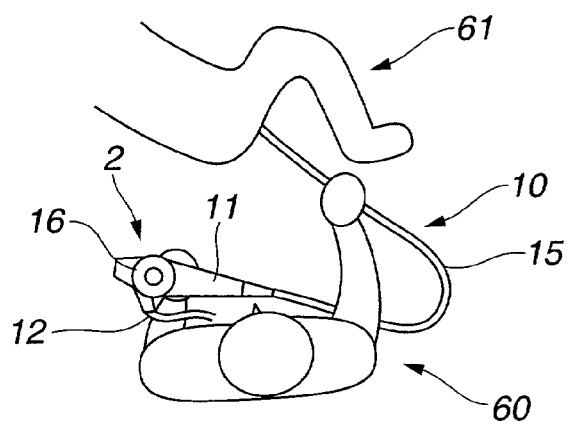
FIG. 7 is an explanatory diagram showing a scene where an operator is inserting an insertion member to a patient with the operator and other things seen from overhead.

Consequently, when the endoscope 2 must be inserted into the large intestine of a patient 61, an operator 60 usually holds, as shown in FIG. 7, the control section 11 with the left hand and holds part of the flexible tube 15 with the right hand. At this time, the flexible tube 15 is so long that the proximal portion of the flexible tube 15 is often bent, though the magnitude of bend varies depending on the operator 60. The flexible tube is bent in a direction close to the up direction.

Therefore, even if the portion of the flexible tube 15 proximal to the predetermined portion of the insertion member, that is, the portion of the insertion member proximal to the predetermined distal portion of 70 cm long thereof is held bent, since the proximal portion of the flexible tube 15 is bent in the up direction during examination as mentioned above, an operator will hardly feel that the inserting smoothness of the insertion member has changed.

As mentioned above, the portion of the flexible tube proximal to the predetermined portion of the insertion member is held bent in consideration of a direction in which the flexible tube is always bent during examination. Therefore, even if the portion of the flexible tube proximal to the predetermined portion of the insertion member is held bent, an operator will not feel that the inserting smoothness of the insertion member has changed.

Moreover, the predetermined portion of the insertion member is settled in the direction of a diagonal of the rectangular tray and is thus substantially straightened. The distal portion of 70 cm or longer of the insertion member can be settled in a substantially straight form, and the sterilization casing can be designed compactly.

If the direction in which the insertion member 10 is bent is limited to the aforesaid down or up direction, the insertion member 10 is always bent in the same direction. After the endoscope is sterilized repeatedly with high-pressure steam, the insertion member 10 may be held bent to a greater extent.

Therefore, tray bodies causing the insertion member to bend in opposite directions may be made available in order to prevent the insertion member from being held bent in one direction. In this case, even after the endoscope is sterilized repeatedly with high-pressure steam, the initial inserting smoothness thereof can be maintained. The direction in which the insertion member is bent is not limited to the up or down direction but may be the right or left direction.

A third embodiment of the present invention will be described with reference to FIG. 8.

An endoscope container for high-pressure steam sterilization in accordance with the present embodiment is a substantially tubular insertion member sheathing member 70 that can be freely attached and detached to/from the insertion member 10 of the endoscope 2.

As illustrated, the insertion member sheathing member 70 consists mainly of a hard pipe portion 71, a coil pipe portion 72, and a fixing member 73. The hard pipe portion 71 is part of the positioning member and is formed with a relatively hard member. The hard pipe portion 71 sheathes and holds the distal portion of 70 cm long of the insertion member 10 of the endoscope 2, that is, the predetermined portion of the insertion member 10 thereof in a predetermined form (substantially straight form). Incidentally, arrow A indicates a point of 70 cm apart from the distal end of the insertion member 10. The coil pipe portion 72 that is flexible sheathes the portion of flexible tube 15 proximal from the distal portion of 70 cm long of the insertion member 10. The flexible tube 15 is a soft part of the insertion member 10. The fixing member 73 is fixed to the proximal end of the coil pipe portion 72.

The fixing member 73 is located, for example, at the position of the therapeutic accessory insertion port 20 formed in the control section 1. Consequently, the insertion member sheathing member 70 is attached to the insertion member 10 as an integral part of the insertion member 10, thus sheathing the insertion member 10.

The thus structured insertion member sheathing member 70 is attached to the insertion member 10 of the endoscope 2 before the endoscope 2 that has been used is sterilized with high-pressure steam. With the insertion member sheathing member 70 thus attached, the endoscope 2 is placed in a sterilizer or the tray 51. At this time, unless the flexible tube 15 of the endoscope 2 is bent, the endoscope 2 cannot be stowed in the tray 51 or a high-pressure steam sterilizer. The portion of the insertion member sheathed with the coil pipe portion 72 of the insertion member sheathing member 70 is therefore bent. At this time, although the flexible tube 15 is bent, the predetermined portion of the insertion member sheathed with the hard pipe portion 71 is hardly bent but held straight.

As mentioned above, the insertion member sheathing member that sheathes the insertion member is composed of the hard pipe portion that sheathes the predetermined portion and the coil pipe portion that sheathes the proximal portion of the flexible tube. When the endoscope is placed in a sterilizer, even if the flexible tube is moderately bent and stowed, the endoscope can be sterilized with high-pressure steam with the predetermined portion held substantially straight. Consequently, the degree of freedom in stowing an endoscope expands. Moreover, deterioration of inserting smoothness derived from high-pressure steam sterilization can be avoided.

According to the present invention, it is apparent that a wide range of embodiments can be formed based on the invention without a departure from the spirit and scope of the invention. Moreover, the present invention will be limited to the appended claims but not restricted by any specific embodiments.

What is claimed is:

1. An endoscope container for high-pressure steam sterilization of an endoscope having a flexible insertion member, the endoscope container being stored in a high-pressure sterilizing device by having at least a part of the insertion member of the endoscope stowed in a curved state, the endoseope container comprising:
   a tray serving as a housing and having a plurality of pores;
   a lid member blocking an opening of the tray and having a plurality of pores; and
   a positioning member, formed in at least one of the tray and lid member, the positioning member being adapted to stow the insertion member of the endoscope during the high-pressure steam sterilization in a predetermined curved form, the curved form having at least a first bend radius corresponding to a distal portion of the insertion member and a second bend radius corresponding to a proximal portion of the insertion member,
   wherein the positioning member is formed such that the first bend radius corresponding to the distal portion of the insertion member is larger than the second bend radius corresponding to the proximal portion of the insertion member and the first bend radius corresponds to the distal portion which is 70 cm or more in length as measured from a distal end of the insertion member.

2. An endoscope container for high-pressure steam sterilization according to claim 1, wherein said positioning member includes a concave predetermined-portion part of said tray.

3. An endoscope container for high-pressure steam sterilization according to claim 1, wherein said positioning member includes a curved wall that is formed on said lid member.

4. An endoscope container for high-pressure steam sterilization according to claim 1, wherein said tray has a handle and a grip for facilitating carrying of said endoscope container.

5. An insertion member sheathing member for storage in a high-pressure sterilizing device by having at least a part of an flexible insertion member of an endoscope stowed in a curved state, the insertion member sheathing member comprising:
   a hard pipe portion, which sheathes a predetermined portion at a distal end side of the flexible insertion member of the endoscope having the distal end side provided with an observation window and holds the predetermined portion in a predetermined curved form, the curved form having a first bend radius corresponding to the predetermined portion; and
   a coil pipe portion that is flexible and sheathes a portion of a flexible tube portion of the flexible insertion member, the flexible tube portion being proximal from the predetermined portion of the flexible insertion member, the flexible tube portion havina a curved form having a second bend radius correspondina to the portion of the flexible tube nortion of the flexible insertion member;
   wherein the first bending radius is substantially laraer than the second bend radius and the predetennined portion is 70 cm or more in length as measured from the distal end side.

6. An endoscope container for high-pressure steam sterilization of an endoscope having a flexible insertion member, the endoscope container being stored in a high-pressure sterilizing device by having at least a part of the flexible insertion member of the endoscope stowed in a curved state, the endoscope container comprising:
   a positioning member being adapted to stow the flexible insertion member of the endoscope during the high-pressure steam sterilization in a predetermined curved form, the curved form having at least a first bend radius corresponding to a distal portion of the flexible insertion member and a second bend radius corresponding to a proximal portion of the flexible insertion member,
   wherein the positioning member is formed such that the first bend radius corresponding to the distal portion of the flexible insertion member is larger than the second bend radius corresponding to the proximal portion of the flexible insertion member and the first bend radius corresponds to the distal portion which is 70 cm or more in length as measured from a distal end of the flexible insertion member.

7. An endoscope container for high-pressure sterilization, the endoscope container being stored in a high-pressure sterilizing device by having at least a part of a flexible insertion member of an endoscope stowed in a curved state, the endoscope container comprising:
   a tray provided with a plurality of pores through which high-pressure steam is led and having an opening for stowing an endoscope having an observation window provided at a distal end of a distal portion of a flexible insertion member thereof which is inserted in a subject; and
   a positioning member formed in the tray for positioning the endoscope in the tray, the positioning member being adapted to stow the flexible insertion member of the endoscope during the high-pressure steam sterilization in a predetermined curved form, the curved form having at least a first bend radius corresponding to the distal portion of the flexible insertion member and a second bend radius corresponding to a proximal portion of the flexible insertion member;
   wherein the positioning member is formed such that the first bend radius is larger than the second bend radius, and said distal portion of the flexible insertion member is 70 cm or more in length as measured from the distal end of the flexible insertion member.

8. An endoscope container for high-pressure sterilization according to claim 7, wherein the positioning member effects the positioning to ensure that a distal portion of approximately 70 cm long of the flexible insertion member is stowed in a substantially straight form or in a curved form.

9. An endoscope container for high-pressure sterilization according to claim 8, wherein the positioning member effects the positioning to ensure that the distal portion of approximately 70 cm long of the flexible insertion member is stowed in a substantially straight form.

10. An endoscope container for high-pressure sterilization according to claim 8, wherein the positioning member includes a concave part formed to stow the distal portion of approximately 70 cm long of the flexible insertion member.

11. An endoscope container for high-pressure steriliza-tion, the endoscope container being stored in a high-pressure sterilizing device by having at least a part of a flexible insertion member of an endoscope stowed in a curved state, the endoscope container comprising:
- a tray provided with a plurality of pores through which high-pressure steam is led and having an opening for stowing an endoscope having an observation window provided at a distal end of a distal portion of a flexible insertion member thereof which is inserted in a subject;
- a lid member that blocks the opening of the tray, the lid member being provided with a plurality of pores through which high-pressure steam is led into the container;
- a positioning member formed in at least one of the tray and the lid member for positioning the endoscope in the tray, the positioning member being adapted to stow the flexible insertion member of the endoscope during the high-pressure steam sterilization in a predetermined curved form, the curved form having at least a first bend radius corresponding to the distal nortion of the flexible insertion member and a second bend radius corresponding to a proximal portion of the flexible insertion member;

wherein the positioning member is formed such that the first bend radius is larger than the second bend radius, and said distal portion of the flexible insertion member is 70 cm or more in length as measured from the distal end of the flexible insertion member.

12. The endoscope container of claim 1, wherein the first bend radius has a substantially infinite radius.

13. The endoscope container of claim 5, wherein the first bend radius has a substantially infinite radius.

14. The endoscope container of claim 6, wherein the first bend radius has a substantially infinite radius.

15. The endoscope container of claim 7, wherein the first bend radius has a substantially infinite radius.

16. The endoscope container of claim 11, wherein the first bend radius has a substantially infinite radius.

* * * * *